United States Patent [19]

Edwards et al.

[11] Patent Number: 4,850,985
[45] Date of Patent: Jul. 25, 1989

[54] OSTOMY SYSTEM UTILIZING A SPLIT RING TO ENGAGE A TWO ELEMENT COUPLING ASSEMBLY

[75] Inventors: John V. Edwards, Surrey, United Kingdom; Frank M. Freeman, Lawrenceville, N.J.

[73] Assignee: E. R. Squibb & Sons, Inc., Princeton, N.J.

[21] Appl. No.: 226,920

[22] Filed: Aug. 1, 1988

[51] Int. Cl.4 ................................................. A61F 5/44
[52] U.S. Cl. ..................................................... 604/339
[58] Field of Search ................................. 604/332–345

[56] References Cited

U.S. PATENT DOCUMENTS

| | | | |
|---|---|---|---|
| 3,339,546 | 9/1967 | Chen | 128/156 |
| 4,192,785 | 3/1980 | Chen et al. | 260/17.4 GC |
| 4,393,080 | 7/1983 | Pawelchak et al. | 428/395 |
| 4,419,100 | 12/1983 | Alexander | 604/339 |
| 4,460,363 | 7/1984 | Steer et al. | 604/336 |
| 4,551,490 | 11/1985 | Doyle et al. | 524/22 |
| 4,559,048 | 12/1985 | Steer | 604/338 |
| 4,642,107 | 2/1987 | Arnone et al. | 604/342 |
| 4,648,875 | 3/1987 | Ferguson | 604/339 |
| 4,664,661 | 5/1987 | Ferguson | 604/342 |
| 4,681,574 | 7/1987 | Eastman | 604/344 |
| 4,685,990 | 8/1987 | Ferguson | 156/253 |
| 4,710,183 | 12/1987 | Steer | 604/344 |

FOREIGN PATENT DOCUMENTS

| | | |
|---|---|---|
| 94613 | 11/1983 | European Pat. Off. . |
| 98718 | 1/1984 | European Pat. Off. . |
| 1274382 | 5/1972 | United Kingdom . |
| 1571657 | 7/1980 | United Kingdom . |
| 2119654 | 11/1983 | United Kingdom . |
| 2115288 | 10/1984 | United Kingdom . |
| 2181652 | 4/1987 | United Kingdom . |
| 2148716 | 9/1987 | United Kingdom . |
| 2179556 | 9/1987 | United Kingdom . |

*Primary Examiner*—Jerome L. Kruter
*Attorney, Agent, or Firm*—Stephen B. Davis

[57] ABSTRACT

An ostomy system in which a third element is employed to absorb pressure when an ostomy pouch is mechanically secured to a body side portion adhesively secured to the body. The third element is a split-ring which can be secured around a body side rib coupling member. The split-ring includes an edge portion that fits in a groove in the outer rib wall and includes an angled outwardly projecting rim so that one or more fingers can be inserted between the rim and the body side surface while the pouch is coupled. Following coupling of the pouch, the split-ring can be removed to leave a two-piece ostomy system in place on the body.

9 Claims, 2 Drawing Sheets

OSTOMY SYSTEM UTILIZING A SPLIT RING TO ENGAGE A TWO ELEMENT COUPLING ASSEMBLY

BACKGROUND OF THE INVENTION

A commercially successful two-piece ostomy system having a body side with a coupling element adapted to mechanically engage a coupling element affixed to an ostomy pouch is described by Steer et al. in U.S. Pat. No. 4,460,363 and United Kingdom Patent No. 1,571,657.

Another commercially available system in order to minimize pressure against the body when a new pouch is affixed to the body side provides a flexible plastic web between the adhesive pad and the body side coupling element as shown by Alexander in U.S. Pat. No. 4,419,100 and United Kingdom Patent No. 2,115,288B. This is also shown by Hunger in European Patent Application No. 94,613. Another commercially available system employs an accordion element between the adhesive pad and the body side coupling element as shown by Jensen in European Patent Application No. 98,718. Steer in U.S. Pat. No. 4,710,183 and United Kingdom Patent Nos. 2,148,716B and 2,179,556B discloses a version of the commercial system described above wherein a flexible chute ring is interposed between the body side coupling element and the adhesive pad. Steer et al. in United Kingdom Patent Application No. 2,119,654A describe another embodiment wherein the body side coupling element has a lateral flange angled away from the adhesive pad and an applicator is inserted between the angled portion of the flange and the pad. Arnone et al. in U.S. Pat. No. 4,642,107 employ a separate accordion element between the body side and bag side coupling element described in the Steer et al. commercial device. Ferguson in U.S. Pat. No. 4,664,661 discloses a modified version of the accordion system and in U.S. Pat. Nos. 4,648,875 and 4,685,990 employs a polymeric foam between the adhesive pad and body side coupling element.

Edwards et al. in United Kingdom Patent Application No. 2,181,652A disclose an ostomy appliance wherein the body side coupling element is spaced from the adhesive pad by a stiff or semi-rigid stepped support member.

Steer in U.S. Pat. No. 4,559,048 discloses an ostomy appliance wherein the coupling includes an annular ring constructed to be snap-fitted to the body side coupling element so that the user can place his thumbs under the ring to support the body side coupling element against inwardly-directed forces applied when fitting a new bag.

Salt et al. in United Kingdom Patent No. 1,274,382 disclose a two piece adhesive ostomy system in which pouches can be changed without discomfort to the user.

SUMMARY OF THE INVENTION

This invention is directed to an improved two piece ostomy system having a body side adhesively secured to the user and a pouch which can be coupled in a releasable manner to the body side. The improvement in the system is a third element which is employed during the coupling step to absorb pressure.

The third element is a split-ring having a relatively flat portion with an inner and outer stepped edges and an outwardly extending rim. The rim extends at an angle of about 35° from the outer stepped edge of the flat surface of the ring. The ring is completely split through both the flat portion and the outwardly extending rim with means provided for releasably securing the split-ring in a completely closed condition. The flat surface of the ring is additionally split radially opposite the complete split so as to enable the split-ring to be further opened.

The pouch side coupling member and the body side coupling member are identical to the commercially available system described by Steer et al. in U.S. Pat. No. 4,460,363 except that a groove is present in the outer peripheral wall of the body side male rib coupling member. This groove is dimensioned to accept the stepped edge of split-ring third element.

When a new pouch or an old pouch is to be coupled or recoupled to the body side, the split-ring third element is opened and slipped around the body side so that the stepped edge fits within the groove in the outer peripheral wall of the male rib coupling member. The split-ring is then secured in its closed condition. The pouch is then coupled by pressing against the body with the thumbs while the fingers are placed between the surface of the adhesive pad and then angled outwardly extending rim. In this way, the force exerted in the coupling step is absorbed by the fingers rather than by the abdomen of the user. After assembly, the split-ring is opened and removed so that the user in effect has a two-piece system in place on the body.

DETAILED DESCRIPTION OF THE INVENTION

Figure 1:
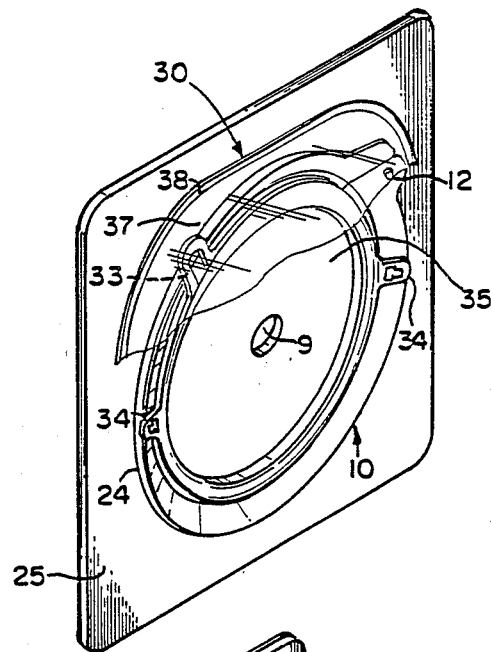
FIG. 1 is perspective view of ostomy appliance of this invention.

This invention is directed to an improvement in two piece ostomy appliances. Such appliances are employed by ostomates to collect bodily waste discharged from a surgically created stoma conventionally located on the abdomen. The term two piece ostomy appliance refers to a system including a body side adhesively secured to ostomate and a pouch which can be removably affixed to the body side. In the immediate post-operative period, the ostomate may experience discomfort when a pouch is coupled to the body side.

This invention is directed to an ostomy system particularly suited for use during the post-operative period. The system consists of a split-ring 10, a body side 20, and a pouch 30. The split-ring is designed to be attached to the body side and provide a space in which the fingers of the user can be inserted so as to absorb the force applied when a pouch is coupled to the body side coupling member. The split-ring is designed so as to be removed after coupling so that the user is left with a flexible, light weight waste collection system on the body.

The body side portion 20 of the ostomy system of this invention is substantially identical to that shown by Steer et al. in U.S. Pat. No. 4,460,363. It consists of an adhesive layer 26 having a thin layer of a polymeric film 25 on one side and a sheet of silicone coated release paper 27 on the other side. A centrally located opening 9 is provided which the ostomate can then enlarge so as to fit the adhesive pad around the stoma. A male coupling member consisting of an upstanding rib 21 of closed loop form and a flange 24 is affixed to the surface of polymeric film 25. The rib includes an inwardly projecting deflectible sealing strip 22 and a rim 23. The outer wall of rib 21 directly above flange 24 has an inwardly extending groove 29.

The adhesive layer 26 can be any pressure sensitive adhesive suitable for use on human skin and capable of supporting weight of the assembled appliance. Preferably, the adhesive consists of an elastomeric substance such as polyisobutylene containing one or more hydrocolloids as taught by Chen in U.S. Pat. No. 3,339,546, by Chen et al. in U.S. Pat. No. 4,192,785, by Pawelchak et al. in U.S. Pat. No. 4,393,080, or it can additionally include a styrene type block copolymer as taught by Doyle et al. in U.S. Pat. No. 4,551,490. The thin polymeric film layer 25 can be polyethylene, polyurethane, or other suitable films.

The pouch portion 30 of the ostomy system of this invention is identical to that shown by Steer et al. in U.S. Pat. No. 4,460,363. In consists of a pouch constructed from two webs of polymeric material 36 and 37 sealed together around their periphery 38. Depending upon the type of ostomy, the pouch can be sealed around the entire periphery, or it can be provided with a drainable opening such as opening 31 which is sealed during use with a clip, or it can be provided with a valve or tap as shown by Steer et al. in U.S. Pat. Nos. 4,300,560 and 4,462,510. The front pouch web 37 includes a stomal opening 35 around which a channel shaped coupling member 32 is attached.

Figure 3:
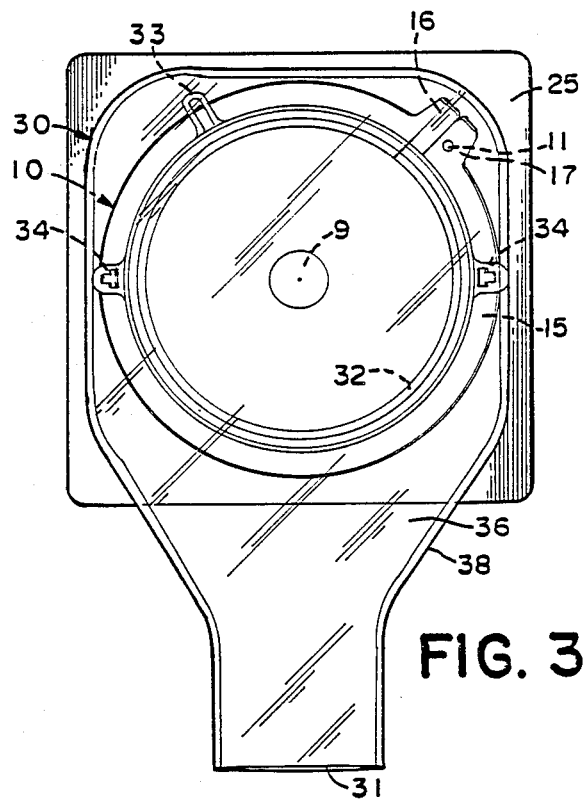
FIG. 3 is a front view showing the ostomy appliance of this invention on the body immediately following the coupling of a pouch.

The channel shaped coupling of closed loop form is dimensioned to fit over standing rib 21 so that the seal strip 22 will deflect toward rib 21. The channel wall mating with rim 23 includes a complementary shaped rim 39. Polymeric webs 36 and 37 can be transparent as shown in FIG. 3 or opaque with transparent pouches being normally preferred during the post-operative hospital period.

Channel shaped coupling member 32 also includes a pull tab 33 to assist in disassembly. Also, a pair of belt lugs 34 are included for the optional attachment of a belt to assist in securing the appliance to the body.

Split-ring 10 is formed of polymeric material and includes a substantially flat surface 13 having an inwardly extending stepped down edge 14. The outer edge of 13 is stepped up to an outwardly extending rim 15. Edge 14 is dimensioned to fit within groove 29 in the outer wall of male coupling rib 21 (see FIGS. 5 and 6).

Figure 2:
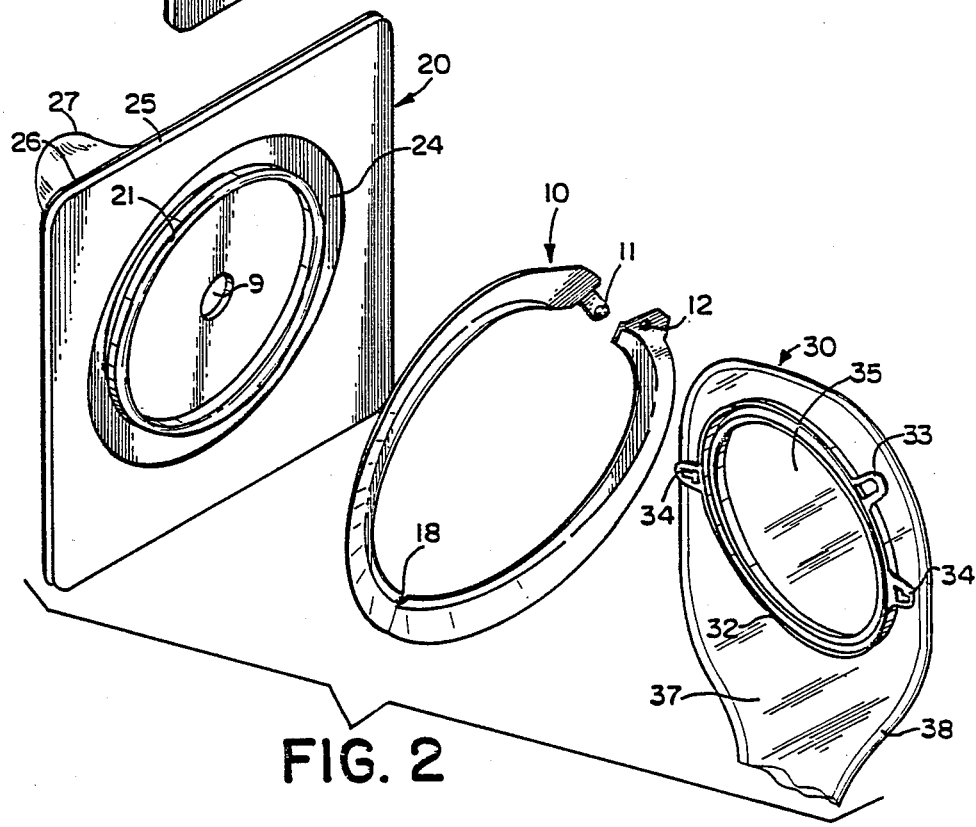
FIG. 2 is an exploded view showing how the three elements of the ostomy appliance of this invention are assembled.

The ring is split as best shown in FIG. 2 so that it can be opened and slipped around male coupling rib 21 on the body side 20. The split-ring is provided with means for temporarily securing the ring in a closed condition. For example, a post 11 can be provided on one side of the split to fit within an aperture 12 in rim 15 on the opposite side of the split. Of course, other means can be employed to secure the split-ring such as snap fitting elements, male and female strips of Velcro, etc. Rim 15 is also provided at the area of the split with ears 16 and 17 so as to enable the user to more easily secure and later separate the split ring. Also, the flat surface 13 is additional split at 18 radially opposite the first split so as to enable the split-ring to be opened a greater distance and facilitate placement of the split-ring around coupling rib 21.

Figure 5:
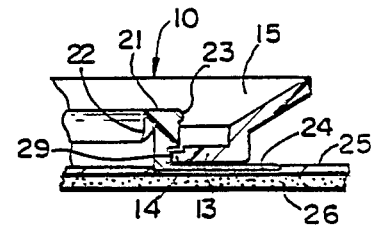
FIG. 5 is a cross-sectional view along line 5—5 of FIG. 4 without the coupled pouch.
Figure 4:
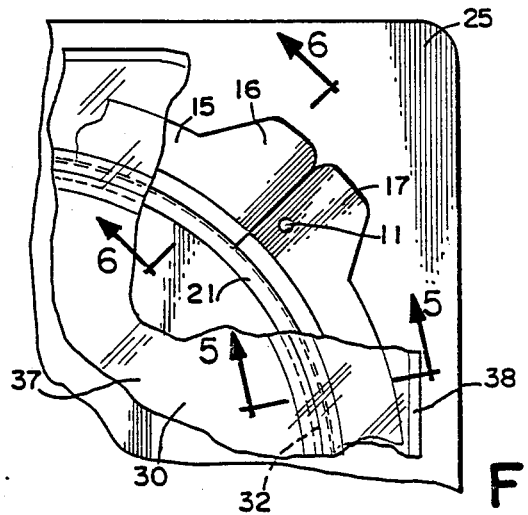
FIG. 4 is an enlarged detailed view of the assembled ostomy appliance in FIG. 3. A break away is provided to show the split-ring in assembled condition.
Figure 6:
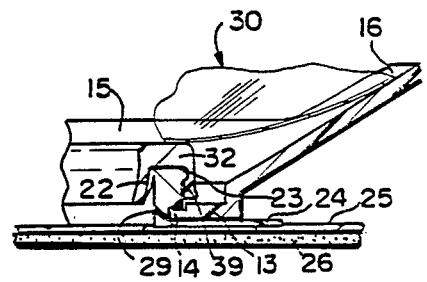
FIG. 6 is a cross-sectional view along line 6—6 of FIG. 4 with the coupled pouch.

As best shown in FIGS. 5 and 6, rim 15 extends outwardly from the outer stepped edge of the flat portion 13 of the split-ring 10 at an angle of about 35°. This angle provides a space between rim 15 and flange 24 affixed to polymeric film 25 in which the user can insert one or more fingers during the coupling step so as to absorb the force which would otherwise be exerted on the abdomen.

The male coupling member is preferably molded as a single piece with rib 21 having deflectable seal strip 22, rim 23, and flange 24. Similarly, channel shaped coupling member 32 including rim 39 is also molded as a single piece. Both coupling members are molded from a suitable polymeric material such as polyethylene.

The split-ring 10 is also preferably molded in a single step from a suitable polymeric material such as nylon.

The ostomy system of this invention is used as follows. An opening is cut or starter hole 9 is expanded so as to fit the adhesive pad of the body side over the stoma of the user. Of course, the opening cannot exceed the inner diameter of coupling rib 21 so that the stoma protruding through the opening is encircled by rib 21. The silicone coated release paper 27 is removed and the adhesive 26 is pressed against the body. Split-ring 10 is opened as shown in FIG. 2 and slipped around rib 21 so that stepped down edge portion 14 fits within groove 29 in the outer rib wall. Ears 16 and 17 are then manipulated so as to secure the split-ring in a closed condition by passing post 11 through aperture 12. The user then couples pouch 30 to the body side by pressing coupling member 32 downward onto rib 21 with the thumbs while absorbing the force with one or more fingers located between angled rim 15 and the surface 25 of the body side portion. After the pouch has been coupled, the split-ring is opened by lifting ear 17. The split-ring is then removed leaving the ostomate with a light weight, flexible, collection system in place on the body. The same procedure is followed when the old pouch is removed and a new pouch is coupled in its place.

What is claimed is:

1. An ostomy system comprising a body side portion, an ostomy pouch portion, and a split-ring means wherein said body side portion comprises an adhesive pad having an opening to fit said pad around the stoma, a male coupling member affixed to said pad about said opening comprising a flange having a rib of closed loop form projecting from said flange outwardly from the body of the user, said rib having a deflectible sealing strip, and the outer rib wall above said flange having a groove, said ostomy pouch formed from two webs of polymeric material sealed together along at least a substantial portion of their periphery, a stomal openign in one of said pouch webs, a channel shaped coupling member of closed loop form affixed to said web about said stomal opening, said channel dimensioned to form a seal with said rib coupling member, and a split-ring means comprising a substantially flat portion having an inwardly extending stepped down edge means dimensioned to fit wwithin said groove in the outer wall of said rib coupling member and an outwardly extending stepped up edge leading to an outwardly projecting angled rim, and means for temporarily securing said split-ring means in a closed condition wherein said ring means can be secured around said rib and the user during the coupling step can place one or more fingers between said outwardly extending angled rim and the surface of said adhesive pad.

2. The ostomy system of claim 1 further comprising a second split in the flat portion and inwardly extending stepped down edge radially opposite said split through said entire ring means.

3. The ostomy system of claim 2 wherein the outwardly extending rim of said split-ring means has ears on both sides of said complete split to facilitate securing said split-ring means in a closed condition.

4. The ostomy system of claim 3 wherein said means for securing said split-ring means in a closed condition is a post projecting from a flange attached to one of said rim ears dimensioned to fit through an aperture in the other rim ear.

5. The ostomy system of claim 1 wherein said rim extends outwardly from said stepped up edge portion of said split-ring means at an angle of about 35°.

6. The ostomy system of claim 1 wherein said adhesive pad has a thin polymeric film to which said male coupling member flange is affixed.

7. The ostomy system of claim 1 wherein said rib coupling member has a rim extending in a direction opposite said deflectible seal strip and one inner wall of said channel coupling member has a complementary shaped rim.

8. The method of coupling an ostomy pouch to a body side portion wherein:

said body side portion comprises an adhesive pad, a male coupling member affixed to said pad comprising a flange having a rib of closed loop form projecting outwardly perpendicularly from said flange, said rib having a deflectible seal strip, and the outer rib wall above said flange having a groove;

said ostomy pouch formed from two webs of polymeric material sealed together along at least a substantial portion of their periphery, a stomal opening in one of said pouch webs, a channel shaped coupling member of closed loop form affixed to said web about said stomal opening;

and a split-ring comprising a substantially flat portion having an inwardly extending stepped down edge and an outwardly extending stepped up edge leading to an outwardly projecting angled rim, and means for temporarily securing said split-ring in a closed condition; wherein the user:

(a) cuts or expands an opening in said adhesive pad so as to fit said pad about the stoma provided that said opening is within the confines of said male loop coupling member so that the stoma protruding through said opening will be encircled by said rib coupling element;

(b) presses the adhesive pad against the body;

(c) expands the split-ring into an open condition and slides the split-ring about said coupling rib so that the stepped down edge of the flat portion of the split-ring is received in the groove in the outer rib wall;

(d) manipulates the split-ring so as to secure the split-ring in a closed condition; and (e) couples the pouch to the body side by pressing the channel member onto the rib member with the thumbs while one or more fingers are placed between the angled rim and the surface of the adhesive pad to absorb the force of coupling.

9. The method of claim 8 further comprising after the pouch has been coupled to the body side:

(f) manipulating said split ring to unsecure the split-ring; and (g) removing the split ring from the body side to leave an assembled two piece ostomy system in place on the body of the user.

* * * * *